(12) United States Patent
Teoh et al.

(10) Patent No.: US 11,318,287 B2
(45) Date of Patent: May 3, 2022

(54) CATHETER HUB WITH FLEXIBLE EXTENDED FLUID CONNECTOR AND RELATED METHODS

(71) Applicant: B. Braun Melsungen AG, Melsungen (DE)

(72) Inventors: Hui Kuun Teoh, Penang (MY); Soo Yong Tan, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 1750 days.

(21) Appl. No.: 14/736,023

(22) Filed: Jun. 10, 2015

(65) Prior Publication Data

US 2016/0361519 A1    Dec. 15, 2016

(51) Int. Cl.
| A61M 25/00 | (2006.01) |
| A61M 25/06 | (2006.01) |
| A61M 39/12 | (2006.01) |
| A61M 39/22 | (2006.01) |
| A61M 39/10 | (2006.01) |

(52) U.S. Cl.
CPC .... *A61M 25/0693* (2013.01); *A61M 25/0097* (2013.01); *A61M 25/0606* (2013.01); *A61M 25/0618* (2013.01); *A61M 39/12* (2013.01); *A61M 39/22* (2013.01); *A61M 2039/1033* (2013.01)

(58) Field of Classification Search
CPC .......... A61M 25/0693; A61M 25/0625; A61M 25/0097; A61M 25/0618; A61M 25/0631; A61M 5/3243; A61M 2005/325; A61M 5/3275; A61M 39/10; A61M 2039/1033; A61M 2039/1061; A61M 2039/1066; A61M 2039/1077; A61M 25/06; A61M 25/0606; A61M 39/12
See application file for complete search history.

(56) References Cited

U.S. PATENT DOCUMENTS

| | | | |
|---|---|---|---|
| 4,326,519 A * | 4/1982 | D'Alo | A61M 25/0637 604/165.04 |
| 4,445,893 A * | 5/1984 | Bodicky | A61M 25/0606 604/165.04 |
| 4,630,616 A * | 12/1986 | Tretinyak | A61B 10/025 600/566 |
| 4,838,282 A * | 6/1989 | Strasser | A61B 10/025 600/567 |
| 5,304,144 A * | 4/1994 | Brimhall | A61M 25/0637 604/165.03 |
| 5,676,656 A * | 10/1997 | Brimhall | A61M 25/0606 604/162 |
| 5,839,715 A * | 11/1998 | Leinsing | A61M 39/1011 251/149.1 |
| 6,213,978 B1 * | 4/2001 | Voyten | A61M 25/0606 604/164.01 |
| 6,443,929 B1 * | 9/2002 | Kuracina | A61B 5/15003 604/192 |

(Continued)

*Primary Examiner* — William R Carpenter
*Assistant Examiner* — William R Frehe
(74) *Attorney, Agent, or Firm* — Klein, O'Neill & Singh, LLP

(57) ABSTRACT

Needle assemblies and related methods are disclosed. The needle assemblies can include a catheter hub and a catheter tube and wherein the catheter hub has a low profile to facilitate attaching the catheter hub to the skins of a patient.

34 Claims, 9 Drawing Sheets

(56) References Cited

U.S. PATENT DOCUMENTS

| | | | | |
|---|---|---|---|---|
| 6,972,002 | B2* | 12/2005 | Thorne | A61M 25/0631 |
| | | | | 604/164.08 |
| 8,939,938 | B2* | 1/2015 | Funamura | A61M 25/0618 |
| | | | | 604/164.08 |
| 10,159,818 | B2* | 12/2018 | Farrell | A61M 5/1626 |
| 2003/0181874 | A1* | 9/2003 | Bressler | A61M 25/0631 |
| | | | | 604/263 |
| 2005/0245963 | A1* | 11/2005 | Kida | A61B 17/12022 |
| | | | | 606/200 |
| 2008/0097344 | A1* | 4/2008 | McKinnon | A61M 25/0637 |
| | | | | 604/263 |
| 2011/0054403 | A1* | 3/2011 | Tanabe | A61M 5/158 |
| | | | | 604/164.01 |
| 2012/0059312 | A1* | 3/2012 | Dikeman | A61M 39/24 |
| | | | | 604/28 |
| 2014/0142538 | A1* | 5/2014 | Hyman | A61F 13/0216 |
| | | | | 604/500 |
| 2014/0276453 | A1* | 9/2014 | Woehr | A61M 25/0606 |
| | | | | 604/246 |
| 2014/0364809 | A1* | 12/2014 | Isaacson | A61M 25/0014 |
| | | | | 604/164.08 |
| 2015/0151085 | A1* | 6/2015 | Tan | A61M 5/3205 |
| | | | | 604/164.08 |
| 2015/0224267 | A1* | 8/2015 | Farrell | A61M 25/0631 |
| | | | | 604/263 |

\* cited by examiner

Ready Position

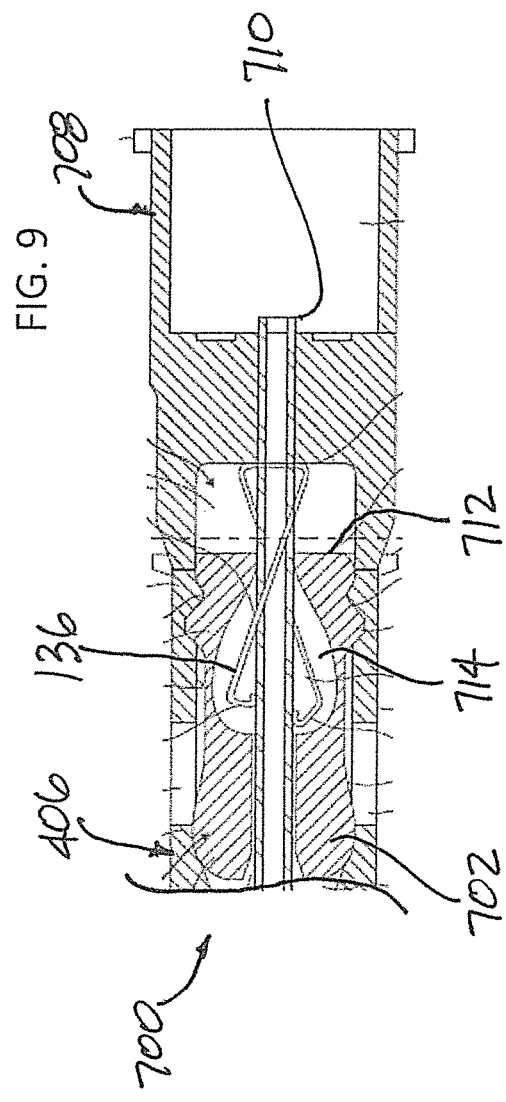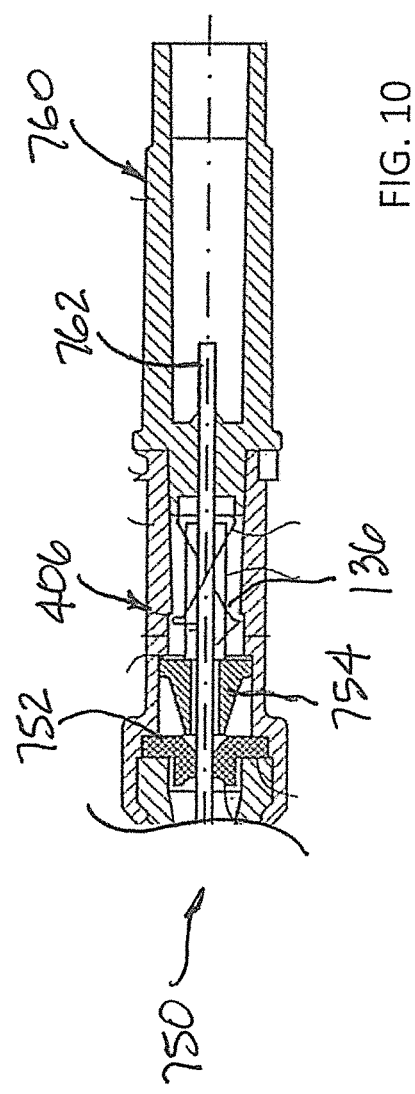

CATHETER HUB WITH FLEXIBLE EXTENDED FLUID CONNECTOR AND RELATED METHODS

FIELD OF ART

The present invention is generally directed to a catheter hub and related methods, and more particularly directed to a low profile catheter hub with a catheter insertion device utilizing needle safety assemblies.

BACKGROUND

The insertion procedure for an IV catheter assembly contains four basic steps: (1) the healthcare worker inserts the needle and catheter together into the patient's vein; (2) after insertion into the vein with the needle point, the catheter is forwarded into the vein of the patient as the healthcare worker pushes the catheter with his or her finger; (3) the healthcare worker withdraws the needle by grasping the needle hub (the end of the needle assembly opposite the sharp needle tip) while at the same time applying pressure to the patient's skin at the insertion site with his or her free hand to stop the flow of blood through the catheter; and (4) the healthcare worker then tapes the exposed end of the catheter (the catheter hub) to the patient's skin and connects it to the source of the fluid to be administered into the patient's vein.

There are several problems with many of the current techniques and catheter systems being used by healthcare workers today. For example, immediately after withdrawal of the needle from the patient's vein, the healthcare worker, who is at this time involved in at least two urgent procedures, must place the exposed needle tip at a nearby location and address the tasks required to finalize the catheterization of the patient. The exposed needle tip creates a danger of an accidental needle stick, which leaves the healthcare worker, and others, vulnerable to the transmission of various dangerous blood-borne pathogens, including AIDS and hepatitis, among others.

Moreover, even once the catheter is taped to the patient's skin, as is customary, the catheter is oftentimes repeatedly accessed by the healthcare worker to connect various instruments to the catheter hub to either withdraw blood, or introduce fluid or other medicines. This repeated connection and disconnection from the catheter hub will oftentimes cause the catheter hub and the connected catheter to move around at the insertion site. This repeated moving can cause a mechanical infection at the catheterization location, including catheter-related bloodstream infections.

Catheter-related bloodstream infection (CRBSI, also called catheter-related sepsis) is defined as the presence of bacteraemia originating from an IV catheter. It is also the most common cause of nosocomial bacteraemia. Overall, CRBSI occurs in about 3% of catheterizations, however, some studies have indicated the incidence may be as high as 16%. In recent studies, this represents 2-30 episodes per 1000 catheter days.

SUMMARY

Aspects of the present disclosure include needle devices or needle assemblies. The needle devices described herein can be a catheter assembly. The catheter assembly can be an over the needle catheter or an IV catheter assembly. The catheter assembly can include a catheter tube attached to a catheter hub, a needle attached to a needle hub and projecting through the catheter hub and the catheter tube in a ready position with a needle tip extending distally of a distal opening of the catheter tube. A fluid port can be positioned next to the catheter hub and connected to the catheter hub by a flexible tube. A valve can be located in the fluid port. The fluid port can have an open proximal end with a female Luer. A needle guard comprising a proximal wall and two arms can be located distally of the proximal wall can be positioned at least in part inside the fluid port. The needle guard can be configured to cover the needle tip to prevent unintended needle sticks. The catheter hub can have two spaced apart grips and the needle hub can be releaseably secured to the catheter hub, such as to the two spaced apart grips. The releasable securement fixes the needle hub relative to the catheter hub in a distal direction. The fluid port can be located between the needle hub and the catheter hub. Movement of the needle hub and the releaseable securement allows a user to grab the needle assembly at a point closer to the needle than otherwise possible.

Aspects of the present disclosure can include a catheter assembly comprising: a catheter hub having a hub body with two grips each comprising a sidewall having a width defined by a space between two sidewalls and a thickness defined by a first exterior surface located above a second lower exterior surface, a proximal end and a distal end and a fluid path extending between the proximal end and the distal end; a catheter tube extending from the distal end of the hub body; a flexible tube extending from the proximal end of the hub body, the flexible tube connected to a fluid port comprising a female Luer; the flexible tube being in fluid communication with the catheter tube; a needle hub having a needle extending through the fluid port, the catheter hub, and the catheter tube; said needle hub comprising wall surfaces removably secured to the catheter hub; and wherein the hub body has a width to thickness ratio greater than 3.

An additional feature of the present disclosure can include a catheter assembly comprising: a catheter hub having a hub body with two grips each comprising a sidewall having a width defined by a space between two sidewalls and a thickness defined by a first exterior surface located above a second lower exterior surface, a proximal end and a distal end and a fluid path extending between the proximal end and the distal end; a catheter tube extending from the distal end of the hub body; a flexible tube extending from the proximal end of the hub body, the flexible tube connected to a fluid port, which is in fluid communication with the catheter tube; wherein the hub body has a width to thickness ratio greater than 3.

The catheter assembly wherein the catheter hub can be substantially rigid.

The catheter assembly wherein the fluid port can include external threads.

The catheter assembly wherein the catheter hub can have a width to thickness ratio greater than 4.

The catheter assembly wherein the catheter hub can have a width to thickness ratio greater than 5.

The catheter assembly can further comprise a needle hub having a needle extending through the catheter hub and a portion of the needle hub can attach directly to the catheter hub.

The catheter assembly wherein a septum can be positioned inside the fluid port and a needle guard can be positioned between the fluid port and the needle hub.

The catheter assembly wherein the portion of the needle hub that can attach to the catheter hub can be a cover having a wall surface with a gap between two edges.

The catheter assembly can further comprise a valve located within an interior cavity of the fluid port.

The catheter assembly can further comprise a needle guard comprising a proximal wall with an opening and two arms located distally of the proximal wall.

The catheter assembly wherein the needle can comprise a change in profile for engaging the proximal wall at the opening.

The catheter assembly can further comprise a valve actuator located inside the interior cavity of the fluid port and proximal of the valve.

The catheter assembly wherein the needle hub can be fixed in a distal direction relative to the catheter hub.

The catheter assembly wherein the needle hub can overlap with the catheter hub such that both can be gripped together.

The catheter assembly wherein the needle hub can comprise a cover comprising a plurality of wall surfaces and wherein the cover can be releasably secured to the catheter hub.

The catheter assembly can further comprise at least one recessed receiving space in contact with the catheter hub.

The catheter assembly wherein the wall surfaces can cover at least 50 percent of a circumference of the fluid port.

The catheter assembly wherein the valve can comprise a proximal projection and wherein the needle guard can contact the proximal projection.

The catheter assembly wherein the valve can include a proximal surface, and wherein the proximal surface can be exposed at a proximal opening of the fluid port for wiping the proximal surface.

The catheter assembly can further comprise a flashback plug having a nose section with an opening.

The catheter assembly can further comprise a septum located in the nose section.

A yet further feature of the present disclosure is a catheter assembly comprising: a low-profile catheter hub having a width that is greater than its thickness; a catheter tube extending distally from the catheter hub; a flexible tube located between the catheter hub and a fluid port to provide fluid communication between the fluid port and the catheter tube; a needle hub releasably connected to the catheter hub and having a needle extending distally from the needle hub and through the catheter hub and the catheter tube; and a needle guard located on the needle and releasably secured to the fluid port.

The catheter assembly wherein the fluid port can be disposed within the needle hub when in a first ready position.

The catheter assembly wherein the needle guard can be disposed within the needle hub and proximally to the catheter hub.

The catheter assembly wherein the needle hub can include a gripping portion defined by raised projections.

The catheter assembly can further include a cover on the needle, and the cover can be releasably connected to the catheter hub or the needle hub.

Aspects of the present disclosure can further include a catheter assembly comprising a low-profile catheter hub having a width that is greater than its thickness; a catheter tube extending distally from the catheter hub; a flexible tube located between the catheter hub and a fluid port to provide fluid communication between the fluid port and the catheter tube; a cover on a needle hub releasably connected to the catheter hub, said needle hub comprising a needle extending in a distal direction through the catheter hub and the catheter tube; and a wall extension on the cover, said wall extension having a width that is less than a width of the cover.

The catheter assembly wherein the cover can have a first cover length measured at the wall extension that is at least 1.04 times longer than a second cover length of the cover.

The catheter assembly can further comprise gripping portions located at a proximal exterior surface of the cover, closer to a proximal edge of the cover than a mid-section on the cover.

BRIEF DESCRIPTION OF THE DRAWINGS

These and other features and advantages of the present devices, systems, and methods will become appreciated as the same becomes better understood with reference to the specification, claims and appended drawings, wherein:

FIG. 9 is a side cross-sectional view of a catheter assembly having a wipeable or swabable blood stop.

FIG. 10 is a side cross-sectional view of a catheter assembly having a valve and a valve actuator.

DETAILED DESCRIPTION

The detailed description set forth below in connection with the appended drawings is intended as a description of presently preferred embodiments of low profile catheter hubs and safety needle assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. For example, the present disclosure illustrates and describes a peripheral venous indwelling catheter; however, the features and benefits disclosed herein are equally applicable to other types of catheters. As denoted elsewhere herein, like element numbers are intended to indicate like or similar elements or features.

Figure 1:
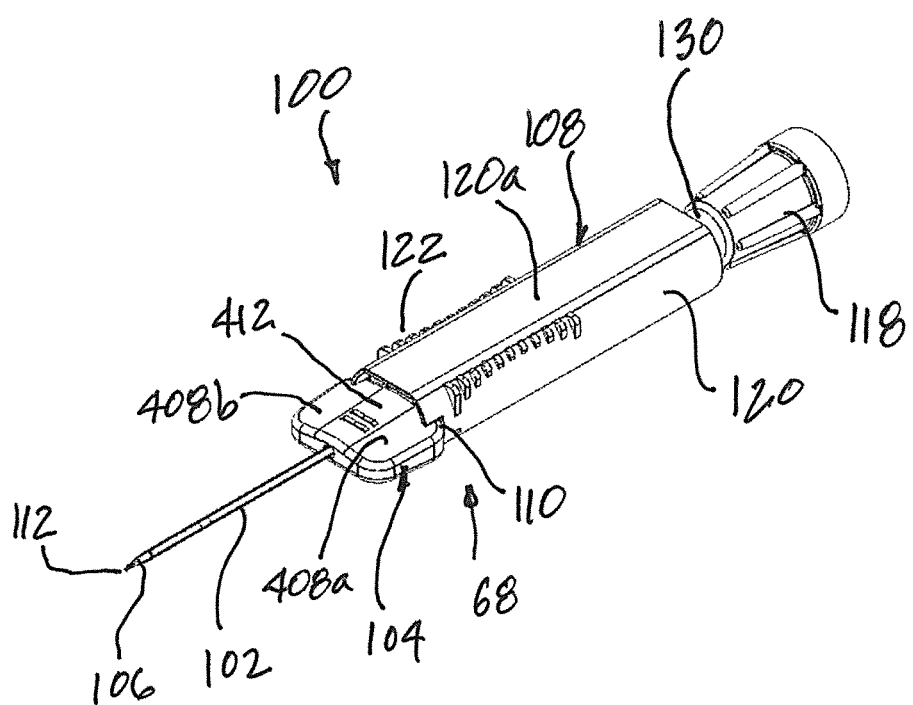
FIG. 1 is an isometric view of an embodiment of an intravascular catheter device in a ready to use configuration.

With reference to FIG. 1, a catheter assembly or more generically a needle assembly 100 is shown comprising a catheter tube 102 extending distally from a catheter hub 104 comprising grip sections or grips 408a, 408b and a central portion 412. A needle 106 extends distally from a needle hub 108 and through the catheter hub 104 and through the catheter tube 102. The needle hub 108 releasably engages a proximal end 110 of the catheter hub 104. The needle 106 includes a sharp distal tip or tip 112 that protrudes from the catheter tube 102 at the distal end thereof. The needle hub 108 includes a flashback plug 118 at its proximal end, which acts as a vent plug. The flashback plug 118 comprises a hydrophobic material, such as a hydrophobic filter, so as to inhibit blood leakage from the proximal end of the needle hub 108 while permitting air to vent.

Figure 2:
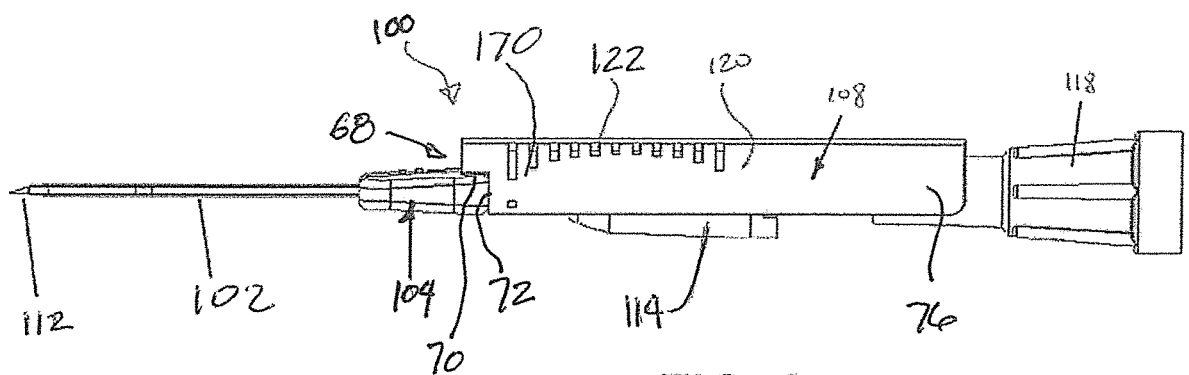
FIG. 2 is a side view of an embodiment of a catheter assembly showing a low profile catheter hub and a needle hub.
Figure 3:
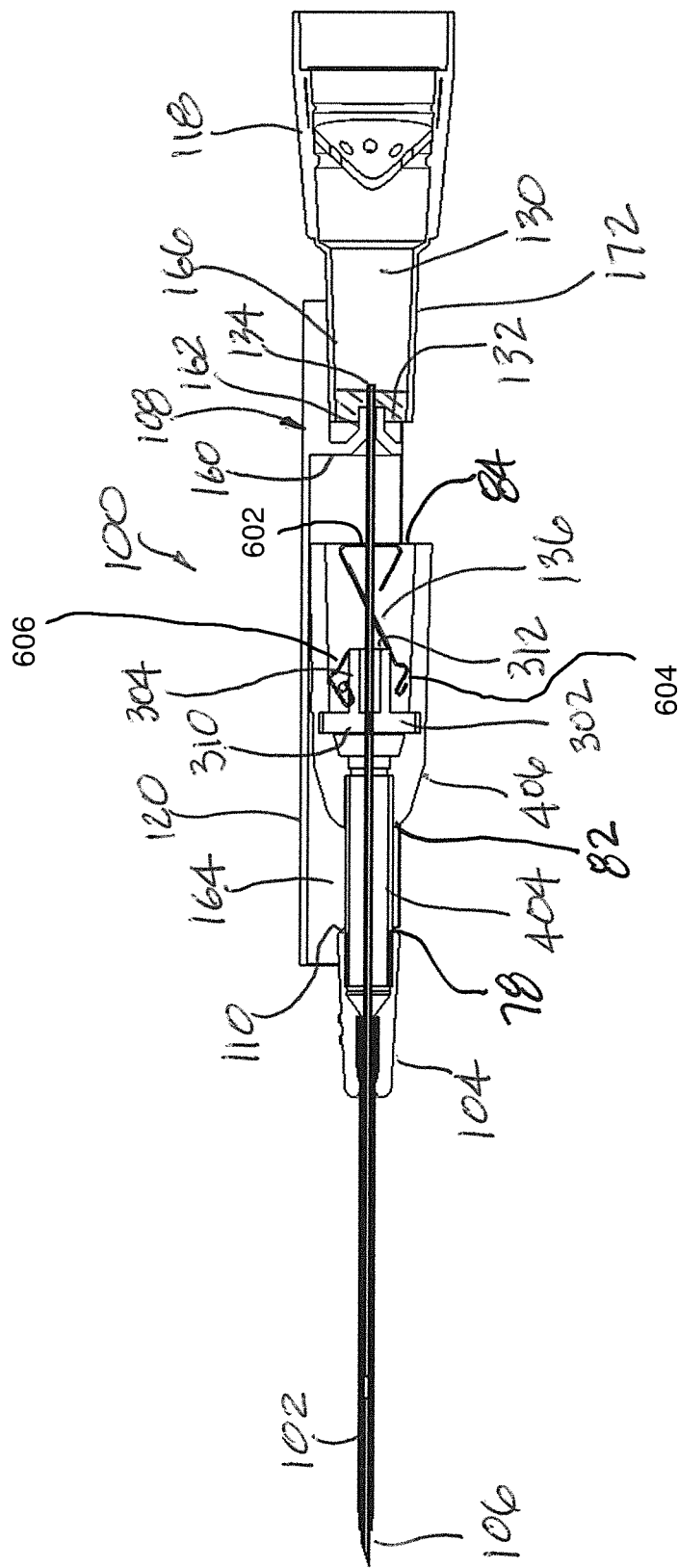
FIG. 3 is across sectional view of the catheter assembly of FIG. 2.

With reference to FIGS. 2 and 3 in addition to FIG. 1, the needle hub 108 comprises a cover 120 and a flange 160 with an anchor post 162 for supporting the proximal end of the needle 106. Relative to the flange 160, the cover 120 has a distal chamber 164 and a proximal chamber 166. The distal chamber 164 of the cover 120 releasably engages with the catheter hub 104 at its proximal end 110 and the proximal chamber 166 receives the flashback plug 118. In one example, the nose section of the flashback plug 118 projects over the anchor post 162 and the needle proximal end and is sealed thereto, such as with a septum. In another example, the proximal chamber 166 is formed as a female Luer with an enclosed body for receiving the nose section of the flashback plug 118.

As shown, the cover 120 has multiple sides, such as a 3-sided cover or more than three sides, but not a continuous circumference. In some example, at least part of the cover can form a continuous circumference. As shown, the cover 120 has wall surfaces 120a that cover approximately 50% to 75% of the circumference of the catheter assembly 100. In other examples, the cover has multiple wall sections or surfaces forming a partial shroud that has a coverage of more than 75% of the circumference of the port, such as up to about 85%, as further discussed below. The cover 120 is releasably connected to the catheter hub 120 by any suitable structure. In some embodiments, the releasable connection is accomplished by one or more indentations in the catheter hub 104, such as detents, a groove, or a pocket, and the cover 120 is configured with a corresponding ridge or protrusion that cooperates with the structure of the catheter hub 104 to connect the two pieces. In other embodiments, there is a friction fit between the catheter hub 104 and the cover 120 with or without detents. In some configurations, an interference between the catheter hub 104 and the cover 120 is provided when they are attached to one another and the two components are inhibited from being further urged toward one another, such as being axially registered to one another. This allows a healthcare worker to hold the cover 120, which is part of the needle hub 108, at a location close to the catheter hub 104 and at a distal end of the cover, for improved leverage to insert the needle tip 112 into a patient during venipuncture.

Figure 5:
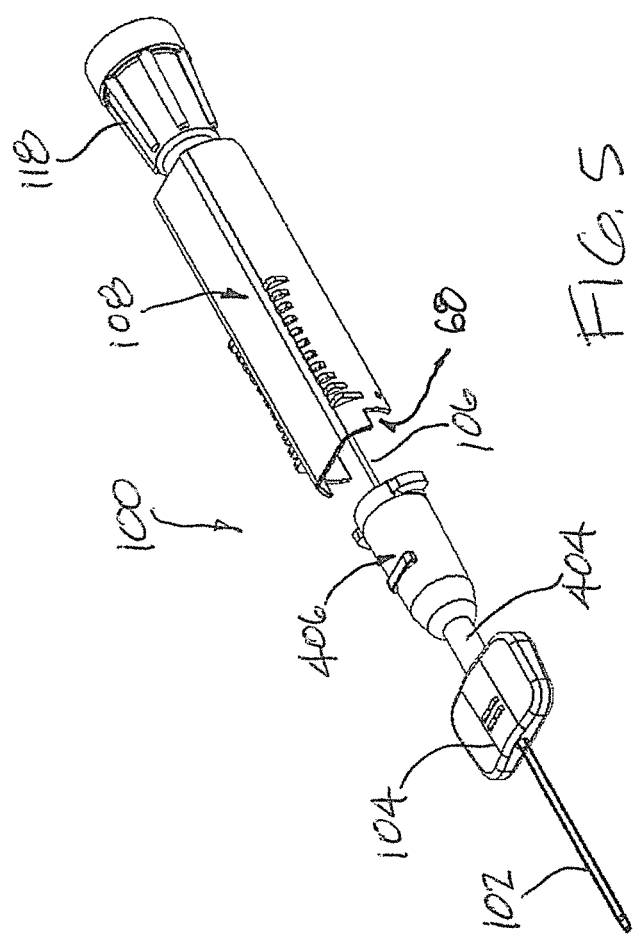
FIG. 5 is an isometric view of a catheter assembly where the needle is in a partially withdrawn position.

As shown in FIGS. 1, 2 and 5, the cover has two recessed receiving spaces 68 at a distal end thereof for contacting or abutting the catheter hub 104. Each receiving space 68 comprises at least one contacting edge. As shown, two or more contacting edges 70, 72 are provided. The two contacting edges 70, 72 abut the catheter hub 104 to fix movement of the cover 120 and hence the needle hub 108 in the distal direction relative to the catheter hub 104. The contacts at the two receiving spaces 68 with the catheter hub 104 establish a reference point so that the trim length of the needle assembly 100, which is the distance between the ground needle bevel of the needle tip 112 and the distal most end of the catheter tube 102, can be set.

As further described below, the releasable connection between the cover 120 and the catheter hub 103 allows a user to grip the needle hub 108 closer to the tip 112 of the needle 106 even when grabbing the needle hub 108 from a location remote from the tip. For example, when performing a venipuncture, a user can grab the needle hub 108 at a proximal point 76 near the flashback plug 118. However, because the cover 120 extends in a distal direction and grip the catheter hub at the two receiving spaces 68, among other connections or other contact points, leverage on the catheter hub 104 is gained by the releasable connection. This in turn provides the user with better control when sticking a patient at the access site. Another benefit of the present needle assembly 100 is the presence of the cover 120 and the benefit of extending the reach of the needle hub 108. For example, although the proximal end of the needle hub 108 is spaced from the catheter hub 104 and a fluid port 406 is located between the two, a user can still grip the needle hub 108 at a location closer to the catheter hub 104 by gripping the cover 120 at a location or point near the catheter hub, such as near grip point 170 (FIG. 2).

Figure 1A:
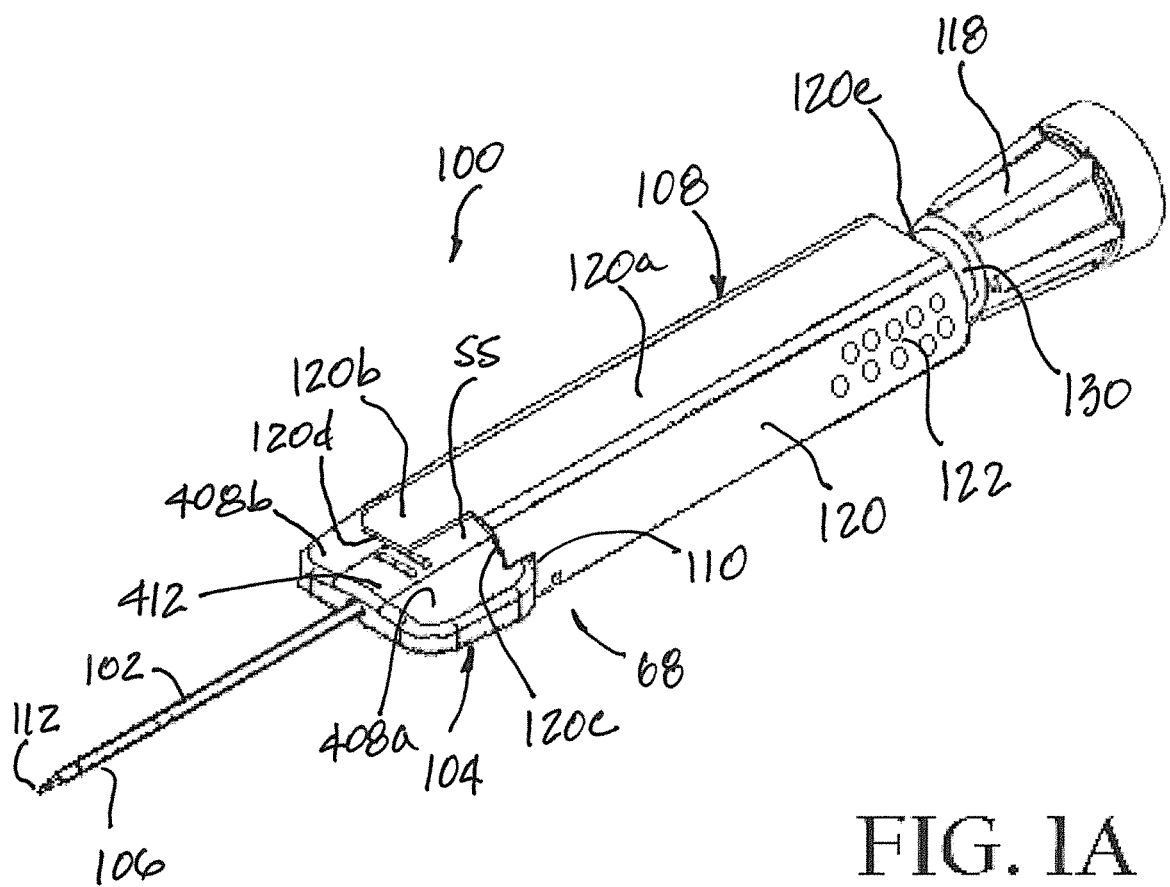
FIG. 1A is an isometric view of an alternative embodiment of an intravascular catheter device in a ready to use configuration.

FIG. 1A shows an alternative catheter assembly 100 provided in accordance with further aspects of the present disclosure. The present catheter assembly 100 is similar to the catheter assembly of FIG. 1 with a few exceptions. In the present embodiment, the wall surfaces 120a of the cover 120 of the needle hub have a wall extension 120b. As shown, the wall extension 120b extends distally of a distal wall edge 120c such that it extends over a section of at least one of the grips 408a, 408b on the catheter hub 104. In an example, the wall extension 120b can also extend over part or all of the central portion 412 of the catheter hub 104. Thus, the distal end of the cover has two distal edge sections 120c, 120d that are offset and defining a cutout 55. In an example, the offset arrangement exposes one of the grips 408a while the other grip 408b is covered by the wall extension 120b. In some examples, the wall extension 120b can be altered to cover a different grip while leaving another or different grip exposed. The shape of the wall extension 120b can be oblong, generally square, generally rounded, semi-circular, semi-oval, or other suitable shape that enables the wall extension to cover at least part of one grip of the catheter hub. Also, in the present embodiment compared to the embodiment of FIG. 1, the gripping portion 122 has been relocated to a proximal position on the cover 120. The gripping portion 122 can comprise ridges, bumps, divots, or other gripping features to facilitate gripping by a user. The gripping portion 122 can be located at a proximal exterior section of the cover closer to a proximal edge of the cover than a mid-section of the cover.

In an example, the wall extension 120b on the cover 120 has a width and wherein the width of the wall extension is less than the width of the cover. In some example, the width of the wall extension 120b is about 25% to about 75% of the width of the cover. In other examples, the width of the wall extension 120b is about 40% to about 50% of the width of the cover. The length of the cover from the proximal edge 120 to the distal edge 120d at the wall extension, called a first cover length, is greater than the length of the cover from the proximal edge 120 to the distal edge 120c at the cutout, called a second cover length. In an example, the first cover length is about 1.04 to 1.2 times longer than the second cover length.

To facilitate catheterization, the cover 120 is configured with a gripping portion 122. The gripping portion 122 can embody a series of grooves, or in some embodiments, is a series of knurls or other gripping features. The gripping portion 122 provides a place for the healthcare worker to adequately grip the needle hub 108 and advance the needle tip 112 during the catheterization procedure, such as near distal grip point 170 shown in FIG. 2. In some preferred embodiments, the gripping portion 122 is a series of grooves or indentations formed in the needle hub cover 120 in which the indentations project inwardly into the interior of the needle hub 108. The inward projections serve to strengthen the cover 120 in that localized area, similar to ribs or reinforcing members, to prevent deformation of the cover when gripped by a healthcare worker. In the embodiments in which the gripping portion 122 is formed as knurls, the outwardly projecting knurls provide some localized reinforcement to the cover 120 to inhibit deformation of the cover when gripped by a healthcare worker. In order to maximize the ease of use, the needle hub 108, such as the cover 120 of the needle hub, should be easily removable from the catheter hub 104 following insertion of the needle 106 and catheter tube 102 into a patient. Accordingly, the reinforcement of the cover 120 allows the cover to resist deformation when the healthcare worker grips and squeezes the cover 120 so tightly that the cover 120 deforms and becomes difficult to remove from the catheter hub 104. Moreover, in some embodiments, the gripping portion 122 is formed such that it has sufficient or adequate clearance or is not directly aligned with the catheter hub 104 so that even if there was slight deformation of the cover 108, it is unlikely to bind with the catheter hub 104. In still other examples, a relatively rigid or hard thermoplastic is used to form the needle hub to ensure sufficient rigidity so that the cover does not deform when gripped.

To facilitate insertion of the catheter assembly 100 of FIG. 1A, a user can grip both the needle hub 108 and the catheter hub 104 at a point closest to the catheter hub 104 by gripping at the wall extension 120b. This allows the user to grip both the wall extension 120b and one of the grips 408b when advancing the needle during insertion. The user can also steady the catheter assembly 100 during insertion by gripping the gripping portion 122 at the proximal location of the cover 120. Once the vein is found and blood flashback is confirmed, the user can change his or her grip on the catheter hub 104 to now grip the other grip 408a without the wall extension to slide the catheter tube further into the vein while withdrawing the needle. In other words, by gripping the other grip 408a, the user does not interfere with the cover as the needle hub is being retracted in the proximal direction to separate from the catheter hub and the fluid port.

Thus, aspects of the FIG. 1A embodiment comprises a catheter assembly 100 comprising a catheter hub with a catheter tube, a fluid port connected to the catheter hub by a flexible tube, and a needle hub having a needle extending through the fluid port, the flexible tube, the catheter hub, and the catheter tube with the needle tip extending distally of a distal end of the catheter tube. The needle hub comprises a cover comprises wall surfaces that overlap or cover approximately 50% to 75% of the circumference of the catheter assembly 100. In other examples, the cover has multiple wall sections or surfaces forming a partial shroud that has a coverage of more than 75% of the circumference of the port, such as up to about 85%, as further discussed below. In an example, a wall extension extends distally of a distal wall edge on the cover to thereby cover or overlap with at least one of the grips on the catheter hub. The wall extension allows a user to grip the catheter hub and the needle hub at a point close to or directly over the catheter hub during insertion of the needle into a patient's vein.

The proximal end of the needle hub 108 preferably carries or supports a flashback plug 118. In some embodiments, the flashback plug 118 has a wall surface defining a flashback chamber 130 in fluid communication with the hollow needle 106. For example, a nose section 172 may project into the proximal chamber 166 and around the proximal end of the needle 106. Upon successful venipuncture, flashback of blood flows through the needle and into the flashback chamber 130, which is viewable to the healthcare worker. A vent filter, such as a hydrophobic filter, is typically placed at a proximal end of the flashback plug 118 to permit venting. In this way, the flashback chamber 130 provides a visual indicator that the healthcare worker has properly and successfully inserted the needle into the patient's vein. The assembly 100 can also provide secondary flashback when the user retracts the needle proximally while the catheter tube 102 is in the patient's vein and viewing blood flow in the annular space between the needle 106 and the catheter tube 102. Of course, the catheter assembly 100 can provide alternative or additional visual cues, such as providing the catheter hub 104, needle hub 108, cover 120, and/or other components out of transparent or semi-transparent materials so the healthcare worker can view flashback of blood through the catheter assembly 100 prior to the blood reaching the flashback chamber 130. The flashback plug 118 can contain a seal 132, such as a septum or a valve through which the proximal end 134 of the needle 106 and/or anchor post 162 pass or passes. The seal 132 is configured to fluidly seal around the needle 106 and/or the anchor post 162 so as to prevent blood from escaping the flashback chamber 130 out the distal end of the nose section 172. The flashback plug 118 may be permanently affixed to the proximal chamber 166 of the cover 120 by any suitable mechanism, such as by gluing, welding, snap-fit, or combinations thereof. The flashback plug 118 can instead be removable from the cover 120. For example, the flashback plug 118 can be removed from the needle hub 108 and subsequently used as a blood sampling source, such as for use to dispense blood samples.

Figure 4:
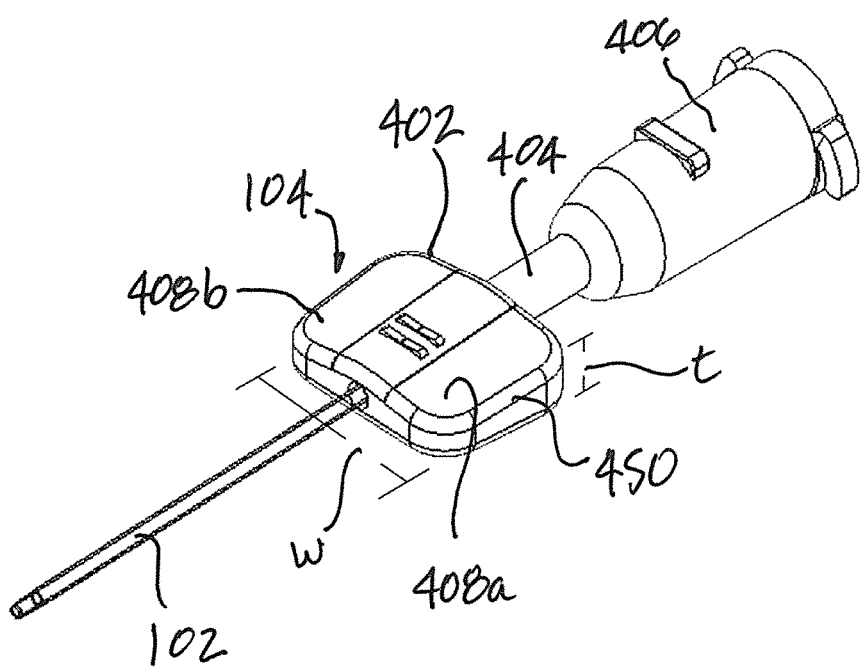
FIG. 4 is an isometric view of one embodiment of a catheter showing a low profile catheter hub, flexible tube and fluid port that can be used with the catheter assembly.

With reference to FIGS. 3 and 4, the catheter hub 104 will be more fully described. The catheter hub 104 has a catheter tube 102 extending distally therefrom. At its proximal end 402, the catheter hub 104 connects to a flexible extension tube or flexible tube 404, which in turn is connected to a fluid port 406, which has a body with an opening having a Luer taper and is commonly known in the art for receiving a male Luer implement, such as an IV fitting, a syringe tip, or an IV adaptor. The open end may also include external threads for threaded engagement with a threaded collar on the male Luer implement. The catheter hub 104 of the present embodiment has a generally flattened rectangular cuboid shape having grips 408a and 408b formed laterally of a central portion 412. The grips 408a, 408b may have rounded or contoured corners and the central portion 412 may be planar in shape or may be slightly undulating. Each grip can include a sidewall 450. The grips 408a, 408b serve at least two important functions: firstly, they provide a gripping surface for the healthcare worker to grab the catheter assembly 100 while inserting the catheter 102, or while removing the needle 106; and secondly, the grips are a rigid and an integral part of the catheter hub 104, and as such, provide exceptional catheter stabilization when placed against the skins of a patient. As previously discussed, the catheter hub 104 may be gripped by simply gripping the cover 120 on the needle hub 108. In some examples, tactile textured material, such as elastomeric inserts or pads, may be added to the exterior surface of the catheter hub 104, such as to the grips 408a, 408b, to provide added gripping benefit.

In some embodiments, the grips are integrally formed with the catheter hub 104, while in other embodiments the grips 408a, 408b are formed separately and attached to the central portion 412. The catheter hub 104 is preferably formed to have a low profile, such that its width w is at least twice its thickness t, which makes the hub body stable and less prone to rolling or tipping. The contour of the catheter hub, looking from an end view, is somewhat rectangular. Thus, the catheter hub 104 can have a shape that is other than round, generally round, or oval, or generally oval. Both sides of the grips 408a, 408b, otherwise known as wings, can also taper downwards to avoid a tenting effect during catheter securement. This allows the catheter hub 104 of the present disclosure to have a low profile with a desired width w to thickness t ratio. In some embodiments, the ratio of the catheter hub 104 width 14' to its thickness t is on the order of 3, or 4, or 5 or more. The width of the catheter hub 104, which can be the distance or measurement between the two sidewalls 450, provides a very stable platform with which to secure the catheter hub 104 to the patient. The thickness can be measured between a first exterior surface and a second exterior surface, which is located opposite the first exterior surface. For example, the second exterior surface can be the surface that contacts the patient's skin and the first exterior surface is the surface opposite the second exterior surface. The low profile with large width to thickness ratio has an increased surface area for contacting the skins compared to traditional prior art having a generally cylindrical body. The low profile also allows traditional catheter securement methods to be used, such as with a flexible transparent medical tape as is well known in the art.

The width of the catheter hub 104, due at least in part to its width to thickness, or height, ratio, resists rotational movement of the hub 104 once it has been secured to the patient. For prior art catheter hubs having a generally round cross-section, the width to thickness ratio is about 1, which makes prior art hubs susceptible to rolling. Moreover, because of its large surface area compared with traditional catheter hubs having generally round hub bodies, the present catheter hub 104 will not tend to slip or move around once secured to the patient. Optionally, two opposed wings may be incorporated with the hub 104 to further increase its width, although not required because of the already relatively wide footprint. In the illustrated embodiment, the lower surface of the catheter hub 104 that contacts a patient is illustrated as generally flat and substantially planar. However, it will be appreciated that the skin surface contact can be improved by forming the patient contact surface of the catheter hub 104 to be curved, such as gradually concave to more closely resemble the curvature of the patient's anatomy at the catheterization site. In an example, an integrated adhesive layer as a lining with peelable release layer can be added to the base of the catheter hub, on the side of the catheter hub 104 that faces the skin. The adhesive layer is useful especially during emergency, whereby before putting on the dressing, the inserted catheter will not be dislodged or easily moved by patient movement. In another embodiment, the catheter hub 104 can be wrapped up, such as coated or molded, with a soft material, such as silicone rubber, at least in the area of the hub 104 that will contact with the patient (such as the central portion and the side portions of the catheter hub) for better patient comfort and to improve catheter stabilization.

As shown in FIGS. 3 and 4, the proximal opening 78 of the catheter hub 104 is sized and shaped to receive the extension tube 404. The opening 78 can be sized and shaped to receive the extension tube 404 in a tight fitting or interference arrangement. The extension tube 404 can be sized as standard IV tubing. In other examples, the opening 78 for receiving the extension tube 404 can have a customized size depending on the size of the extension tube, such as depending on the outside diameter of the extension tube. The extension tube 404 and the catheter hub 104 can be connected using an interference fit, solvent bonding and/or other conventional means, such as by gluing.

FIG. 3 shows a relatively large gap between the end surface near the proximal opening 84 of the fluid port and the flange 160. In practice, this gap can be relatively small or the two surfaces can even abut. Thus the total length of the needle hub does not need to be as long as shown when this gap is reduced or eliminated. In one example, to maintain the described trim length, the abutting contact is between the needle hub 108 and the catheter hub 104 due to the assembly tolerances at the connection points of the flexible tube and the catheter hub and between the flexible tube and the fluid port.

The fluid port 406 is connected to the catheter hub 104 via the flexible extension tube 404. The distal opening 82 of the fluid port 406 can be configured in the same manner as the proximal opening 78 of the catheter hub 104 for receiving the extension tube 404. The flexible extension tube 404 provides fluid communication between the fluid port 406 and the interior of the catheter hub 104, which is in fluid communication with the catheter tube 102. By connecting a fluid source to the fluid port 406 rather than directly to the catheter hub 104, a healthcare worker can administer fluid, nutrients, or the likes to the patient and can withdraw blood from the patient as is generally known in the art. The flexible extension tube 404 also isolates the catheter hub 104 from movement of the fluid port 406. Thus, the extension tube 404 functions as a dampening device for absorbing movement and twisting possibly induced on the catheter hub 104 by when the fluid port 406 is moved, purposefully or otherwise. For example, after the catheter hub 104 is affixed to the patient's skin by an adhesive tape or dressing and the fluid port 406 is connected to an IV adaptor, movement to the fluid port 406 during the connection can be absorbed by the extension tube 404. The healthcare industry has become increasingly concerned about catheter movement after catheterization. Studies show that movement of the catheter tube, catheter hub, access site, or combinations thereof post venipuncture can lead to issues such as phlebitis and serious CRBSIs. The flexible extension tube 404 allows a healthcare worker to access the fluid port 406 with minimal disturbance or dislocation of the catheter hub 104 and catheter tube 102. It is believed that the secure attachment afforded by the grips 408a, 408b in combination with the flexible extension tube 404 will greatly reduce the incidence of nosocomial bacteraemia.

The fluid port 406 is preferably configured with an internal blood control septum 302 of any suitable design. One particular effective embodiment utilizes a protruding ring septum that cooperates with a needle guard 136 to protect the healthcare worker. A preferable blood control septum 302 is also externally swabable, such as those disclosed in co-pending U.S. Publication application No. 2014/0276453 A1, filed Jul. 25, 2013, the contents of which are expressly incorporated herein by reference. In the present blood control septum 302 (FIG. 3), a proximal projection 304 is provided that is easily accessible from the rear of the fluid port 406 with a swab coated with a sterilizing agent to easily sterilize the blood control septum 302 in between repeated access to the fluid port 406. The proximal projection 304 projects proximally from a main septum body 310 and presents an end surface 312 near the proximal opening of the fluid port 406. When a male medical implement, such as male Luer tip, a syringe tip, or IV adaptor and the like, is inserted into the opening of the fluid port 406, the end surface 312 is pushed distally forward by the male medical implement to open one or more slits formed through the main body 310, which opens a fluid pathway through the septum 302 to facilitate fluid flow from a fluid through the fluid port, the extension tube, and the catheter hub and catheter tube. In an example, the end surface 312 includes one or more pusher extensions that extend in a proximal direction towards the proximal opening 84 of the fluid port 406. The one or more pusher extensions can be located in the Luer taper area of the fluid port 406 so that when a male Luer tip is inserted into the fluid port, the tip pushes on the one or more pusher extensions to advance the proximal projection 304 in the distal direction to open the one or more slits of the main body 310.

In some embodiments, an actuator or activator is provided inside the proximal opening 84 of the fluid port 406, to be pushed by a male Luer tip against the end surface 312 the septum for fluid flow. For example, the proximal projection 304 on the septum 302 may be located inside the fluid port and out of reach of a male Luer tip when the male Luer tip is inserted into the opening 84 of the fluid port. In that situation, an actuator or activator may be slidably positioned proximally of the septum 302 and be pushed by the male Luer tip into the end surface 312 of the proximal projection to open the septum. Exemplary valves and actuators are disclosed in U.S. Pat. No. 8,333,735, the contents of which are expressly incorporated herein by reference. If a needle guard 136 is used with a needle assembly 100 with a valve actuator, the valve actuator can have a gap to accommodate the needle guard 136 in the ready to use position.

Figure 6:
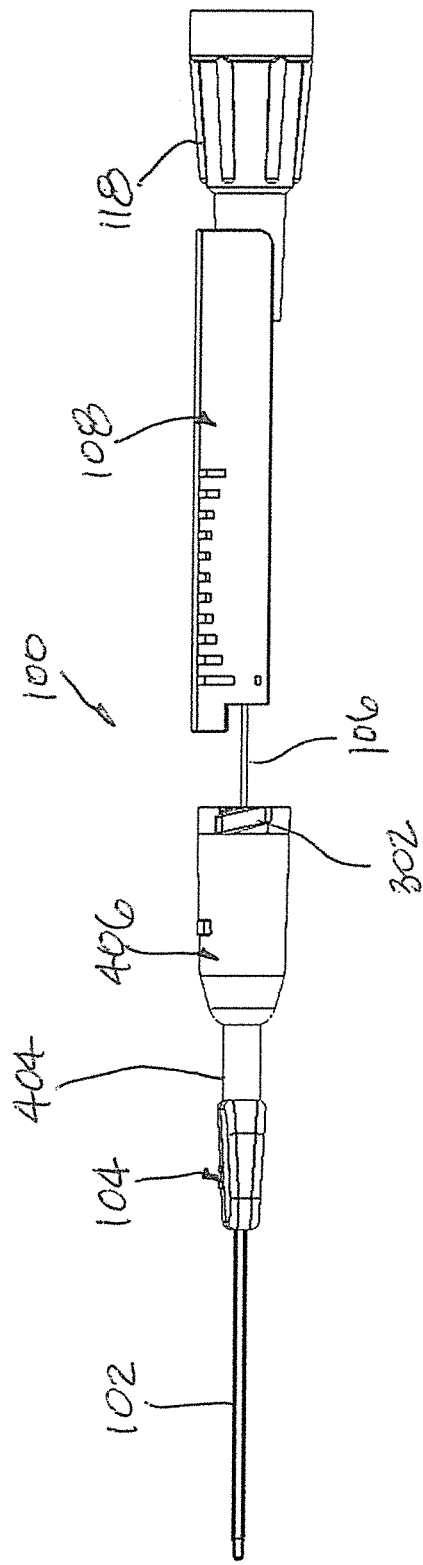
FIG. 6 is a side view of FIG. 5.

With reference to FIGS. 5 and 6 in addition to FIG. 3, the catheter assembly 100 is shown during catheterization with the needle 106 partially withdrawn from the catheter 102, such as following successful venipuncture. During removal of the needle 106, the needle guard 136 (FIG. 3) remains with the fluid port 406. As shown, the needle guard 136 has a proximal wall 602 with a perimeter defining an opening, such as a proximal opening, therein sized to accommodate the needle 106. The needle guard 136 further has two arms 604, 606 each having an end biased against the blood control septum 302 in a ready position. As shown, the needle 106 and needle guard 136 only minimally contact one another at the opening in the proximal wall 602. The two distal end walls are spaced from the needle and rest against the proximal projection 302. There is a change in profile, such as a bulge or crimp (not shown), formed on the needle 106 proximal of the needle tip, as is known in the art. The change in profile is disposed distally of the needle guard 136 when in the ready position as illustrated in FIGS. 1-3. As the needle 106 is retracted sufficiently out of the catheter tube 102 and the needle tip enters the interior cavity of the fluid port 406, the change in profile on the needle engages the perimeter defining the opening on the proximal wall of the needle guard 136 and since the change in profile is larger than the opening in the proximal wall 602, the withdrawing needle pulls on the needle guard displaces the needle guard 136. As the needle guard 136 moves in the proximal direction by the change in profile, the two arms 604, 606 on the needle guard 136 slide proximally off the blood control septum 302 and close over the needle tip 112 to prevent inadvertent needle sticks with the sharp tip 112, which is more clearly shown in FIGS. 7 and 8.

Figure 7:
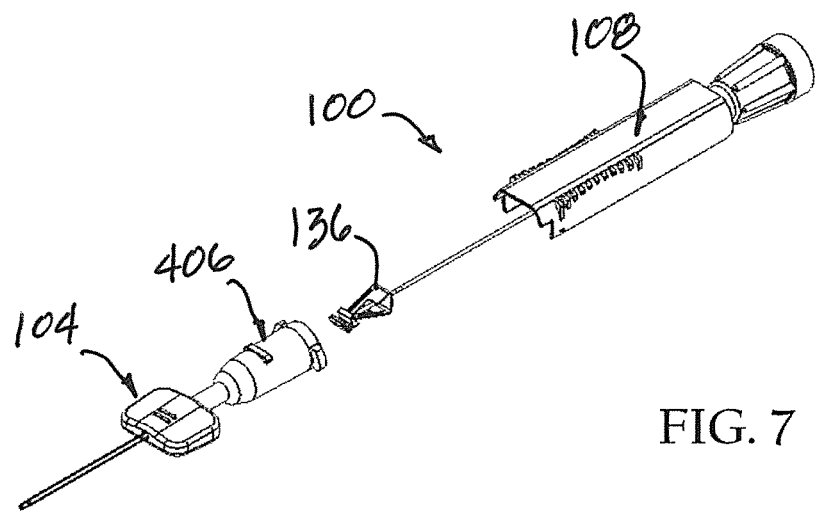
FIG. 7 is an isometric view of an embodiment of a catheter assembly showing the needle fully withdrawn and the needle safety device in place.
Figure 8:
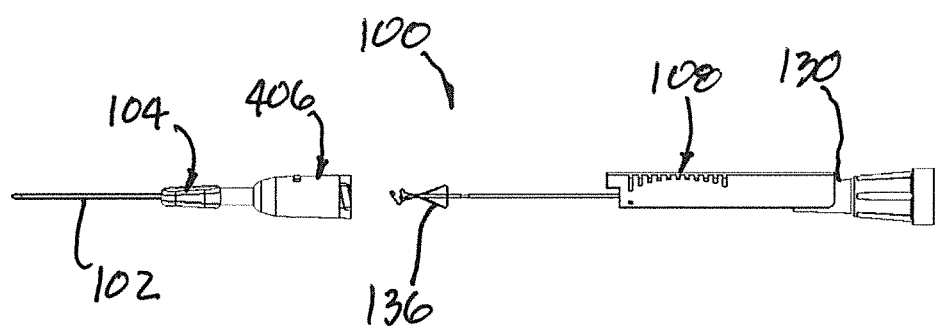
FIG. 8 is a side view of the catheter assembly of FIG. 6 with the needle further retracted and the needle guard protecting the tip of the needle.

With reference to FIGS. 7 and 8, the catheter assembly 100 is shown in a fully withdrawn position. As the needle 106 is withdrawn out of the catheter hub 104 and the fluid port 406, the needle guard 136 becomes dislodged from its purchase within the fluid port 406 and closes over the needle tip 112 thus providing automatic actuating protection against inadvertent needle sticks.

To illustrate the use of the advantages described herein, reference to FIGS. 1 and 7 best illustrate the device in the ready position and in the withdrawn or protective position, respectively. A healthcare worker grasps the needle hub 108 preferably at the gripping portion 122, such as near the gripping point 170 (FIG. 2) on the cover 120. Notably, the gripping portion 122 is located in close proximity to the catheter hub 104 despite portions of the needle hub being located well-spaced from the catheter hub 104 as is separated by a fluid port 406. This allows the healthcare worker to maintain very good control over the needle 106 and the catheter tube 102 during catheterization. Optionally, the healthcare worker can also grasp the catheter hub 104 at the grips 408a, 408b to provide additional stability or leverage during catheterization. Once a suitable site is selected, the healthcare worker advances the needle and catheter tube into the patient. Upon successful venipuncture, blood will flow through the needle 106 and into the flashback chamber 130 signifying to the healthcare worker that at least the needle 106 is properly placed. To ensure that the catheter tube 102 is properly positioned within a vein, secondary flashback can be employed, as discussed above.

At this point, the healthcare worker can completely withdraw the needle hub 108 by continuing to grip the gripping portion 122 and moving the needle hub 108 in a proximal direction relative to the catheter hub 104 by holding onto the catheter hub 104 at the grips 408a or 408b to keep it in place. As the needle 106 moves clear of the fluid port 406, the needle guard 136 will automatically activate and encompass the needle tip 112 to prevent unwanted secondary needle sticks. The healthcare worker can then use transparent tape, or other suitable adhesives or device, to securely affix the catheter hub 104 to the patient's skin. Alternatively, a release layer is removed from the bottom of the catheter hub 104 to expose an adhesive layer, which is then pressed against the skin to more firmly fix the catheter hub to the patient. The catheter hub 104 is much wider than it is thick, which provides the catheter hub 104 with a relatively large surface area in contact with the patient for very stable securement to the patent. In cooperation, the flexible extension tube 404 allows the healthcare worker to access the fluid port 406 without much fear of disturbing the catheter hub 104 or the puncture site. In a similar, but alternative approach, once the catheter tube is properly placed, the healthcare worker can immediately secure the catheter hub 104 in place with a suitable adhesive, and after the catheter hub is secured, then proceed to withdraw the needle to complete catheterization.

Thus, aspects of the present disclosure is understood to include a catheter assembly comprising a catheter hub having a catheter tube, a fluid port connected to the catheter hub by an extension tube, and a needle hub having a needle projecting through the fluid port, the extension tube, the catheter hub, and the catheter tube. The needle hub comprises wall surfaces that extend over the fluid port, the extension tube, and at least part of the catheter hub and removably engaged to the catheter hub. In some examples, the needle hub comprises a cover having wall surfaces that extend over the fluid port, the extension tube, and at least part of the catheter hub. The wall surfaces of the needle hub that extends preferably have at least one opening or slot to keep the needle port, the extension tube, the catheter hub, or combinations thereof exposed and not covered. The releasable engagement between the cover of the needle hub and the catheter hub allows the needle assembly to be firmly gripped, such as firmly gripping the catheter hub, during catheterization despite the needle hub being spaced from the needle hub by a fluid port.

A further aspect of the present disclosure is a catheter assembly having a wide width to thickness ratio, in the order 3, or 4, or 5 or more width to thickness, such as the height of the body forming the catheter hub. Thus, the disclosed catheter hub is stable and has a much lower tendency to roll as compared to a prior art catheter hub having a generally round body with a width to height ratio of about 1.

Another aspect of the present disclosure is securement feature for use with the stable catheter hub having a wide width to height ratio. The securement device can comprise an integrated adhesive layer provided on an underside surface of the catheter hub that faces the patient's skin, preferably with a peelable release layer. Alternatively or in addition thereto, securement tape may be applied over the upper surface of the catheter hub to provide added support from unwanted hub movement. With the catheter hub secured, movement to the fluid port, if any during use, is absorbed by the extension tube and minimizes movement at the catheter hub and the access site.

Yet another aspect of the present disclosure is a valve or septum located inside a fluid port. In an example, the valve or septum is located at a location inside the fluid port that still allows the proximal surfaces of the valve or septum to be wiped or cleaned. A valve actuator is not required to open such valve or septum. In some example, the valve or septum is located inside the interior cavity of the fluid port such that a valve actuator is required to open the valve or septum.

In some examples, a needle guard comprising a proximal wall with an opening and at least one arm is provided inside the fluid port with the valve or septum. A change in profile on the needle can engage a perimeter defining the opening on the proximal wall to remove the needle guard along with the needle following successful venipuncture.

A second septum may be provided with a vent plug for sealing around the needle or for providing a seal around a proximal end of the needle. The vent plug is incorporated to enable blood flash back and the septum is provided to limit or prevent leakage between the vent plug and the needle hub.

With reference now to FIG. 9, a catheter assembly 700 having a wipeable or swabable blood stop 702 is shown. The catheter assembly 700 is shown without a catheter hub, which can be similar to the catheter hub 104 of FIGS. 1-8 and discussed elsewhere herein. The present catheter assembly 700 is shown with a fluid port 406 having the blood stop 702 located in an interior cavity thereof. The fluid port 406 can be connected to the catheter hub via a flexible tube, similar to the embodiments of FIGS. 1-8. A needle 710 extends from a needle hub 708 through the blood stop 702 and through the fluid port in a ready to use position. The needle also extends through a flexible tube that connects to the fluid port, a catheter hub, and a catheter tube with a needle tip extending distally of a distal end of the catheter tube. The needle hub 708 can include a similar cover as that shown in FIGS. 1 and 1A.

The blood stop 702 can be similar to the blood stop shown and described in U.S. Publication application No. 2014/0276453 A1, which was previously incorporated herein by reference. The wipeable blood stop 702 is located in the interior cavity of the fluid port 406 and has a proximal surface 712 this is generally aligned with or even with the open proximal end of the catheter hub for wiping or cleaning the proximal surface 712, such as with a swab, a cotton ball, a prep pad, a swab pad, or the likes. The blood stop has an open interior cavity 714 for accommodating a needle guard 136, similar to the needle guard of FIG. 3, for covering the needle tip of the needle to prevent inadvertent needle sticks.

With reference now to FIG. 10, a catheter assembly 750 having a valve 752 and a valve actuator 754 is shown. The catheter assembly 750 is shown without a catheter hub 756, which can be similar to the catheter hub 104 of FIGS. 1-8 and discussed elsewhere herein. The present catheter assembly is shown with a fluid port 406 having the valve 752 and the valve actuator 754 located therein. The fluid port 406 of FIG. 10 can be connected to the catheter hub via a flexible tube, similar to the embodiments of FIGS. 1-8. A needle hub 760 with a needle 762 extends through the valve 752, the valve opener or actuator 754, the fluid port 406, a flexible tubing that connects to the fluid port, a catheter hub, and a catheter tube (not shown) with the needle tip extending distally of a distal end of the catheter tube in a ready to use position. The needle hub 708 can include a similar cover as that shown in FIGS. 1 and 1A.

A needle guard 136, similar to the needle guard of FIG. 3, is located in-line with the valve actuator 754. As shown, the needle guard 136 is located at a proximal actuating end 764 of the valve actuator 754, which has a gap for accommodating the needle guard. The valve, valve opener, and needle guard of FIG. 10 are shown and described in U.S. Pat. No. 8,333,735, which was previously incorporated herein by reference. As earlier indicated, when a valve is positioned sufficiently distal within the interior cavity of a fluid port 406, a valve opener or actuator may be required to actuate the valve. In one example, the valve and valve actuator of FIG. 10 are usable with the fluid port 406 of FIG. 3.

Methods of manufacturing and of using the catheter assemblies discussed herein are understood to be within the scope of the present invention.

The above description presents various embodiments along with the process of making and/or using them, in such full, clear, concise, and exact terms as to enable any person skilled in the art to which it pertains to make and use this invention. This invention is, however, susceptible to modification and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A catheter assembly comprising:
   a catheter hub having a hub body, the hub body comprising:
   two spaced apart sidewalls,
   a width defined by a space between the two spaced apart sidewalls,
   a thickness defined by a first exterior surface located above a second lower exterior surface, the thickness being a dimension orthogonal to the width,
   a proximal end, a distal end, and a fluid path extending between the proximal end and the distal end;
   a catheter tube extending from the distal end of the hub body of the catheter hub;
   a fluid port comprising a body with a proximal opening;
   a flexible tube with a flexible body located between the hub body and the fluid port and connected to both the hub body and the fluid port; the flexible tube being in fluid communication with the catheter tube and the fluid port and configured to flex when the fluid port moves relative to the hub body;

a needle hub having a needle extending through the fluid port, the catheter hub, and the catheter tube; said needle hub comprising wall surfaces removably secured to the catheter hub;

wherein the hub body has a width to thickness ratio greater than 3; and wherein the needle is removable from the fluid port without terminating fluid communication between the fluid port and the catheter tube.

2. The catheter assembly of claim 1, wherein the catheter hub is substantially rigid.

3. The catheter assembly of claim 1, wherein the proximal opening of the fluid port is a female Luer with external threads.

4. The catheter assembly of claim 1, wherein the hub body has a width to thickness ratio greater than 4.

5. The catheter assembly of claim 1, wherein the hub body has a width to thickness ratio greater than 5.

6. The catheter assembly of claim 1, further comprising a valve located within an interior cavity of the fluid port.

7. The catheter assembly of claim 6, further comprising a needle guard comprising a proximal wall with an opening and at least one arm located distally of the proximal wall.

8. The catheter assembly of claim 7, wherein the needle comprises a change in profile for engaging the proximal wall at the opening.

9. The catheter assembly of claim 7, wherein the valve comprises a proximal projection and wherein the needle guard contacts the proximal projection.

10. The catheter assembly of claim 7, wherein the valve has a proximal surface, and wherein the proximal surface is exposed at the proximal opening of the fluid port.

11. The catheter assembly of claim 6, further comprising a valve actuator located inside the interior cavity of the fluid port and proximal of the valve.

12. The catheter assembly of claim 1, wherein the needle hub is fixed in a distal direction relative to the catheter hub.

13. The catheter assembly of claim 12, wherein the needle hub comprises a cover comprising the wall surfaces and wherein the cover is releasably secured to the catheter hub.

14. The catheter assembly of claim 13, further comprising at least one recessed receiving space in contact with the catheter hub.

15. The catheter assembly of claim 13, wherein the wall surfaces cover at least 50 percent of a circumference of the fluid port.

16. The catheter assembly of claim 1, wherein each sidewall has a grip and wherein each grip has a dimension that is greater than a diameter of the needle.

17. The catheter assembly of claim 1, wherein each sidewall of the two spaced apart sidewalls has a grip and each grip has a taper that tapers from the distal end to the proximal end of the catheter hub.

18. The catheter assembly of claim 1, further comprising a needle guard located at least in part inside a proximal end of the fluid port.

19. The catheter assembly of claim 1, wherein a septum is positioned inside the fluid port.

20. A catheter assembly comprising:
a catheter hub having a hub body, the hub body comprising:
two spaced apart sidewalls,
a width defined by a space between the two spaced apart sidewalls,
a thickness defined by a first exterior surface located above a second lower exterior surface, the thickness being a dimension orthogonal to the width,
a proximal end, a distal end, and a fluid path extending between the proximal end and the distal end;
a catheter tube extending from the distal end of the hub body;
a fluid port comprising a body with a proximal opening;
a flexible tube with a flexible body located between the hub body and the fluid port and connected to both the hub body and the fluid port so that the fluid port is connected to the hub body via the flexible tube, the flexible tube being sized and shaped to flex when the fluid port moves relative to the hub body;
wherein the hub body has a width to thickness ratio greater than 2; and
wherein a needle is removable from the catheter tube without separating the fluid port from the catheter hub.

21. The catheter assembly of claim 20, further comprising a needle hub wherein the needle extends through the catheter hub and the catheter tube.

22. The catheter assembly of claim 21, wherein a septum is positioned inside the fluid port and a needle guard is positioned between the fluid port and the needle hub.

23. The catheter assembly of claim 21, wherein the portion of the needle hub that attaches to the catheter hub is a cover having a wall surface with a gap between two edges.

24. A catheter assembly comprising:
a low-profile catheter hub having a width and a thickness, wherein the width is greater than the thickness;
a catheter tube extending distally from the catheter hub;
a fluid port located proximally and spaced from the catheter hub, the fluid port comprising a body with a proximal opening;
a flexible tube with a flexible body projecting into a proximal end of the catheter hub and projecting into a distal end of the fluid port to provide a conduit for fluid communication between the fluid port and the catheter tube;
a needle hub having a needle with a needle tip extending distally from the needle hub, the needle hub releasably connected to the catheter hub with the needle extending through the catheter hub and the catheter tube in a ready to use position;
a septum or a valve located inside the fluid port for restricting flow out the proximal opening of the fluid port; and
wherein the fluid port is connected to the catheter hub via the flexible tube when the needle is removed from the catheter tube and the catheter hub.

25. The catheter assembly of claim 24, wherein the fluid port is disposed within the needle hub when in a first ready position.

26. The catheter assembly of claim 24, wherein the needle guard is disposed within the needle hub and proximally to the catheter hub.

27. The catheter assembly of claim 24, wherein the needle hub has a gripping portion defined by raised projections.

28. The catheter assembly of claim 24, wherein a cover of the needle hub is releasably connected to the catheter hub.

29. The catheter assembly of claim 24, wherein a needle guard is positioned inside the fluid port.

30. The catheter assembly of claim 24, the catheter assembly further comprising a needle guard, wherein the needle guard has a surface located to a side of the needle and movable distal of the needle tip in a protective position to prevent unintended needle stick.

31. A catheter assembly comprising:
a low-profile catheter hub having a width and a thickness, wherein the width is greater than the thickness;
a catheter tube extending distally from the catheter hub, the catheter tube having a distal opening;
a fluid port comprising a body with a female Luer opening;
a flexible tube having a flexible body located between and connected to the catheter hub and the fluid port to provide a conduit for fluid communication between the fluid port and the catheter tube, the flexible tube being configured to flex when the fluid port moves relative to the catheter hub;
a cover on a needle hub extending distally over the fluid port and the flexible tube to releasably contact the catheter hub, said needle hub comprising a needle having a needle tip extending in a distal direction through the catheter hub, the fluid port, and the catheter tube;
wherein the flexible tube projects through a distal opening of the fluid port; and
wherein the cover and the needle hub are both separable from the catheter hub, the fluid port, and the catheter tube in a used position, where the female Luer opening of the fluid port is exposed for receiving a male Luer.

32. The catheter assembly of claim 31, wherein the cover has a first cover length measured at a wall extension that is at least 1.04 times longer than a second cover length of the cover.

33. The catheter assembly of claim 31, further comprising gripping portions located at a proximal exterior surface of the cover, closer to a proximal edge of the cover than a mid-section on the cover.

34. The catheter assembly of claim 31, wherein the flexible tube projects through a proximal opening of the catheter hub.

* * * * *